US010823745B2

(12) United States Patent
Yamashita et al.

(10) Patent No.: US 10,823,745 B2
(45) Date of Patent: Nov. 3, 2020

(54) BLOOD TEST KIT AND BLOOD ANALYSIS METHOD

(71) Applicant: FUJIFILM Corporation, Tokyo (JP)

(72) Inventors: Seiji Yamashita, Ashigarakami-gun (JP); Haruyasu Nakatsugawa, Ashigarakami-gun (JP); Susumu Osawa, Tokyo (JP); Shinya Sugimoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 196 days.

(21) Appl. No.: 15/862,700

(22) Filed: Jan. 5, 2018

(65) Prior Publication Data

US 2018/0128845 A1    May 10, 2018

Related U.S. Application Data

(63) Continuation of application No. PCT/JP2016/070007, filed on Jul. 6, 2016.

(30) Foreign Application Priority Data

Jul. 6, 2015    (JP) ................. 2015-135067
Jul. 6, 2016    (JP) ................. 2016-133961

(51) Int. Cl.
*A61B 5/15*    (2006.01)
*B01L 3/00*    (2006.01)
(Continued)

(52) U.S. Cl.
CPC ....... *G01N 33/96* (2013.01); *A61B 5/150022* (2013.01); *A61B 5/150343* (2013.01);
(Continued)

(58) Field of Classification Search
CPC ........ A61B 5/150022; A61B 5/150015; A61B 5/150007; A61B 5/15; A61B 5/150343;
(Continued)

(56) References Cited

U.S. PATENT DOCUMENTS 2,697,945 A    12/1954  Dovas
5,700,652 A *  12/1997  Tadano ................... C12Q 1/34
                                                          435/14

(Continued)

FOREIGN PATENT DOCUMENTS

CN    101701962 A    5/2010
CN    102053068 A    5/2011
(Continued)

OTHER PUBLICATIONS

Kyowa Medex Co., Ltd., WO 03/005039 A1, English Machine Translation, obtained by STIC at the USPTO, obtained on Sep. 18, 2019, pp. 1-69. (Year: 2019).*
(Continued)

*Primary Examiner* — Christine T Mui
(74) *Attorney, Agent, or Firm* — Sughrue Mion, PLLC

(57) ABSTRACT

An object of the present invention is to provide a blood test kit and a blood analysis method capable of performing a blood test with a small amount of blood at high accuracy by visualizing a volume of blood collection and keeping the volume constant. According to the present invention, a blood test kit including a diluent solution for diluting components of a blood sample; and at least one transparent container for storing the components of the blood sample and the diluent solution, in which at least one constituent component included in the blood test kit is marked with a graduation for measuring the components of the blood sample and a liquid volume of the diluent solution, is provided.

13 Claims, 4 Drawing Sheets

(51) Int. Cl.
*G01N 33/96* (2006.01)
*G01N 33/48* (2006.01)
*G01N 33/49* (2006.01)
*G01N 1/38* (2006.01)

(52) U.S. Cl.
CPC .... *A61B 5/150755* (2013.01); *B01L 3/50825* (2013.01); *G01N 33/48* (2013.01); *G01N 33/491* (2013.01); *A61B 5/150351* (2013.01); *B01L 3/50* (2013.01); *B01L 2200/0631* (2013.01); *B01L 2200/0689* (2013.01); *B01L 2300/042* (2013.01); *B01L 2300/047* (2013.01); *B01L 2300/049* (2013.01); *B01L 2300/0681* (2013.01); *B01L 2400/0478* (2013.01); *G01N 1/38* (2013.01)

(58) Field of Classification Search
CPC ..... A61B 5/150755; B01L 3/502; B01L 3/50; B01L 3/00
USPC ........................................................ 422/430
See application file for complete search history.

(56) References Cited

U.S. PATENT DOCUMENTS

| | | | |
|---|---|---|---|
| 2001/0055784 A1 | 12/2001 | Noda et al. | |
| 2002/0052008 A1 | 5/2002 | Mahant et al. | |
| 2002/0153316 A1 | 10/2002 | Nanba et al. | |
| 2003/0175167 A1 | 9/2003 | Takanori et al. | |
| 2007/0274865 A1 | 11/2007 | Bouboulis | |
| 2011/0020195 A1* | 1/2011 | Luotola | A61B 10/0045 422/512 |
| 2016/0011150 A1* | 1/2016 | Onuma | G01N 27/44791 204/451 |

FOREIGN PATENT DOCUMENTS

| | | | | |
|---|---|---|---|---|
| GB | 1105367 A | | 3/1968 | |
| JP | S52-57688 U | | 4/1977 | |
| JP | 2000-046825 A | | 2/2000 | |
| JP | 2001-330603 A | | 11/2001 | |
| JP | 2002-538458 A | | 11/2002 | |
| JP | 2003-161729 A | | 6/2003 | |
| JP | 2003-270239 A | | 9/2003 | |
| JP | 2009-109196 A | | 5/2009 | |
| JP | 2009-122082 A | | 6/2009 | |
| JP | 2014-141829 | * | 7/2014 | ....... G01N 27/44791 |
| JP | 2015-105936 A | | 6/2015 | |
| WO | WO 2003/005039 | * | 1/2003 | ............. G01N 33/72 |
| WO | WO 2011/065212 | * | 6/2011 | ............. G01N 33/49 |
| WO | 2015/189961 A1 | | 12/2015 | |

OTHER PUBLICATIONS

Osawa et al, WO 2011/065212, English Machine Translation, obtained by STIC at USTPO, obtained on Sep. 18, 2019, pp. 1-20. (Year: 2019).*
Susumu Osawa et al., "Revolution of medical services at home using a small amount of blood collected from the fingertip," Clinical Testing, May 15, 2015, pp. 397-404, vol. 59, No. 5.
International Search Report of PCT/JP2016/070007 dated Oct. 4, 2016.
Written Opinion issued by the International Bureau in corresponding International Application No. PCT/JP2016/070007, dated Oct. 4, 2016.
International Preliminary Report on Patentability issued from the International Bureau in counterpart International Application No. PCT/JP2016/070007, dated Aug. 3, 2017.
Office Action dated Sep. 11, 2018, issued by the Japanese Patent Office in counterpart Application No. 2016-133961.
Office Action dated Jan. 28, 2019 from European Patent Office in counterpart European Application No. 16 821 431.0.
Office Action dated Mar. 18, 2019, from the Chinese Patent Office in counterpart Chinese Application No. 201680039611.4.
Extended European Search Report dated Jun. 1, 2018, from the European Patent Office in counterpart European Application No. 16821431.0.
Communication dated Feb. 28, 2019 from the European Patent Office in European application No. 16821431.0.
"7.2. Messen and Dosieren flassiger oder gelöster Stoffe", in: Egon Fanghünel et al., "Einführung in die chemische Laboratoriumspraxis", 1992, Deutscher Verlag für Grundstoffindustrie, Leipzig, ISBN: 3-342-00394-4, pp. 99-112 (17 pages).
Office Action dated Sep. 18, 2019, from the China National Intellectual Property Administration in counterpart Chinese Application No. 201680039611.4.
Office Action dated Feb. 18, 2020, from the China National Intellectual Property Administration in counterpart Chinese Application No. 201680039611.4.

* cited by examiner

BLOOD TEST KIT AND BLOOD ANALYSIS METHOD

CROSS-REFERENCE TO RELATED APPLICATIONS

This application is a Continuation of PCT International Application No. PCT/JP2016/070007 filed on Jul. 6, 2016, which claims priority under 35 U.S.C § 119(a) to Japanese Patent Application No. 2015-135067 filed on Jul. 6, 2015 and Japanese Patent Application No. 2016-133961 filed on Jul. 6, 2016. Each of the above application(s) is hereby expressly incorporated by reference, in its entirety, into the present application.

BACKGROUND OF THE INVENTION

1. Field of the Invention

The present invention relates to a blood test kit and a blood analysis method for analyzing a target component in a blood sample.

2. Description of the Related Art

As blood collection, generally, there are general blood collection in which a qualified person such as a doctor collects blood from the vein using a syringe, and self-blood collection in which a subject to be tested pricks his finger and the like using a blood collection needle so as to collect blood.

The blood collected by the general blood collection is transported to a medical institution or a test institution in a sealed state in a blood collection container, and tests are performed therein. In a case where the blood is transported without separating blood cells and blood plasma, tests are performed after a medical institution or a test institution performs centrifugation to separate the blood into blood cells and blood plasma. In addition, in the self-blood collection which is performed by a subject to be tested, the collected blood is separated into blood cells and blood plasma by a separation membrane, and the blood is transported to a test lab in a separated state, and then tests are performed therein.

JP2001-330603A discloses a quantitative analysis method in which an amount of a target component to be analyzed in a sample is measured, an amount of a normal component originally and homeostatically present in the sample, other than the target component, is measured, a volume of the sample is determined from the amount of this normal component and a known concentration of the normal component in the sample, and therefore a concentration of the target component to be analyzed in the sample is determined from the volume of the sample and the amount of the target component to be analyzed.

JP2003-161729A discloses a method for testing a blood sample collected by self-blood collection, and specifically discloses a method for quantitatively determining a component to be quantitatively determined in a biological specimen, the method including 1) step of preparing a specimen for quantitation consisting of an unknown volume of a biological specimen containing a component to be quantitatively determined which is collected without quantitatively determining the volume thereof, and a certain volume of an aqueous solution containing a certain amount of an indicator substance, 2) step of obtaining a dilution factor (a) of the biological specimen from a concentration ($C_1$) of the indicator substance in the aqueous solution of a certain volume which contains a certain amount of the indicator substance, and a concentration ($C_2$) of the indicator substance in the specimen for quantitation, 3) step of obtaining a concentration (Y) of the component to be quantitatively determined in the specimen for quantitation, and 4) step of determining the component to be quantitatively determined in the biological specimen from the dilution factor (a) of the biological specimen obtained in 2), and the concentration (Y) of the substance to be quantitatively determined in the specimen for quantitation obtained in 3).

In addition, JP2009-122082A discloses that a small volume of blood is collected from a human or an animal using a blood dilution quantitative instrument, and after dilution of the blood, or without dilution, a certain volume thereof is supplied to another instrument or container or is directly supplied to a reagent. Furthermore, JP2009-109196A discloses a method for quantitatively determining a concentration of a component to be quantitatively determined in a biological specimen by utilizing an absorbance of an indicator substance in an aqueous solution for dilution.

Meanwhile, in a case where a subject to be tested collects a blood sample, the blood is collected by using a lancet equipped with a small blade, and is used for quantitatively determining a concentration of an arbitrary component in the blood, but generally, it is required to collect 100 µL or more of a blood sample.

SUMMARY OF THE INVENTION

In the method of JP2001-330603A, there were problems that analysis accuracy deteriorates, the result varies, and therefore the stability of a target component to be analyzed is not secured sufficiently, or that a concentration of sodium ions or chloride ions cannot be used as an external standard.

In the method of JP2003-161729A, in a case where there is a variation in a volume of blood collection, and the collection volume is small, there were problems that a dilution ratio of a diluted standard substance decreases, and the reliability of test accuracy deteriorates because a blood component amount itself is decreased. In addition, in the method of diluting with a buffer solution, a biological component is stored in a buffer solution at physiological conditions of pH 7.4, and thus is excellent in stability during transportation, but because a specimen is added to a buffer solution to which the standard substance was added, a dilution ratio of a standard substance is small, and there is a problem that with addition of only a small amount of the specimen, a measurement error is likely to occur.

As described above, in order to perform a blood test with a small volume of the blood at high accuracy, even the methods disclosed in JP2001-330603A or JP2003-161729A were not sufficient to ensure test accuracy.

Meanwhile, blood collection is an invasive action that damage the skin and depending on the person, there is a case of feeling uncomfortable staring at the red color of blood. Therefore, it is common to have desires for collecting the blood as soon as possible and stopping the blood flowing out from the wound. In accordance with such circumstances, the blood is not always collected in a constant volume and varies in many cases. The large variation in a volume of blood collection results in a deterioration of accuracy of a dilution factor, and therefore visualizing a volume of blood collection and keeping the volume constant are desired.

An object to be solved by the present invention is to provide a blood test kit and a blood analysis method capable of performing a blood test with a small amount of blood at high accuracy by visualizing a volume of blood collection and keeping the volume constant.

As a result of intensive studies to solve the object described above, the inventors of the present invention have found that the object described above can be solved by a blood test kit including a diluent solution for diluting components of a blood sample, and at least one transparent container for storing the components of the blood sample and the diluent solution, in which at least one constituent component included in the blood test kit is marked with a graduation for measuring the components of the blood sample and a liquid volume of the diluent solution, and therefore have completed the present invention. That is, according to the present invention, the following inventions are provided.

(1) A blood test kit, comprising: a diluent solution for diluting components of a blood sample; and at least one transparent container for storing the components of the blood sample and the diluent solution, in which at least one constituent component included in the blood test kit is marked with a graduation for measuring the components of the blood sample and a liquid volume of the diluent solution.

(2) The blood test kit according to (1), in which the graduation includes at least a graduation for measuring a liquid volume of a diluent solution which does not contain the components of the blood sample.

(3) The blood test kit according to (1) or (2), in which the constituent component is at least one transparent container for storing the components of the blood sample and the diluent solution.

(4) The blood test kit according to (3), in which the transparent container has a portion of which an interior cross-sectional area is smaller than that of other portions, and the portion of which the interior cross-sectional area is smaller than that of other portions is marked with the graduation.

(5) The blood test kit according to (4), in which a portion of which an interior cross-sectional area is smallest in the transparent container is marked with the graduation.

(6) The blood test kit according to any one of (1) to (5), in which the components of the blood sample are blood plasma components separated from the blood sample by a separation means.

(7) The blood test kit according to any one of (1) to (6), in which the blood test kit is for analyzing a concentration of a target component in the components of the blood sample by using a normal component homeostatically present in the blood, and the diluent solution does not contain the normal component.

(8) The blood test kit according to any one of (1) to (6), in which the blood test kit is for analyzing a concentration of the target component in the components of the blood sample by using a normal component homeostatically present in the blood and for verifying the analysis, and the diluent solution does not contain the normal component.

(9) The blood test kit according to (7) or (8), in which the normal component is a component selected from the group consisting of sodium ions, chloride ions, total protein, and albumins.

(10) The blood test kit according to any one of (1) to (9), in which the diluent solution contains a normal component not present in the blood, and the blood test kit is for analyzing a concentration of the target component in the components of the blood sample by using the normal component not present in the blood.

(11) The blood test kit according to (10), in which the normal component not present in the blood is glycerol 3-phosphate or lithium.

(12) The blood test kit according to any one of (1) to (11), in which the diluent solution is a buffer solution having a buffering action within a pH range of pH 6.5 to pH 8.0.

(13) The blood test kit according to any one of (1) to (12), in which the diluent solution is a diluent solution including an amino alcohol compound selected from the group consisting of 2-amino-2-methyl-1-propanol, 2-ethylaminoethanol, N-methyl-D-glucamine, diethanolamine, and triethanolamine, and including a buffering agent selected from the group consisting of 2-[4-(2-hydroxyethyl)-1-piperazinyl] ethanesulfonic acid also called HEPES, N-tris(hydroxymethyl)methyl-2-aminoethanesulfonic acid also called TES, 3-morpholinopropanesulfonic acid also called MOPS, and N,N-bis(2-hydroxyethyl)-2-aminoethanesulfonic acid also called BES.

(14) A blood analysis method which uses a blood test kit including a diluent solution for diluting components of a blood sample and at least one transparent container for storing the components of the blood sample and the diluent solution, the method comprising: a step of selecting a specimen containing the blood sample components of a predetermined amount or more which have been determined in advance, as an analysis target specimen so as to exclude a specimen containing the blood sample components of less than the predetermined amount from the analysis target specimen; and a step of analyzing the blood by using the specimen containing the blood sample components which have been selected from the above step.

(15) The blood analysis method according to (14), in which the blood test kit is the blood test kit according to any one of (1) to (13), and the specimen containing the blood sample components of the predetermined amount or more which have been determined in advance is selected by using a graduation.

(16) The blood analysis method according to (14) or (15), in which the components of the blood sample are blood plasma components separated from the blood sample by a separation means.

(17) The blood analysis method according to any one of (14) to (16), in which a dilution ratio of the components of the blood sample is calculated by the following Formula 1, and a concentration of a target component to be analyzed in the diluent solution is multiplied by the dilution ratio so as to analyze the concentration of the target component in the components of the blood sample, $$(A+C)/(B+D)$$ Formula 1 in the formula, A represents a measurement absorbance of the diluent solution containing an internal standard substance, B represents an absorbance obtained by subtracting an absorbance of the diluent solution by which the components of the blood sample is diluted from A, C represents a measured absorbance of the solution in which a concentration of sodium ions, as a homeostatic substance, is 142 mmol/L, and D represents an absorbance of sodium ions in the diluent solution by which the components of the blood sample is diluted.

(18) The blood analysis method according to any one of (14) to (17), in which the analysis is performed using the blood of 10 µl or more and 70 µl or less.

An object of the present invention is to provide a blood test kit and a blood analysis method capable of performing a blood test with a small amount of blood at high accuracy by visualizing a volume of blood collection and keeping the volume constant.

DESCRIPTION OF THE PREFERRED EMBODIMENTS

Figure 1:
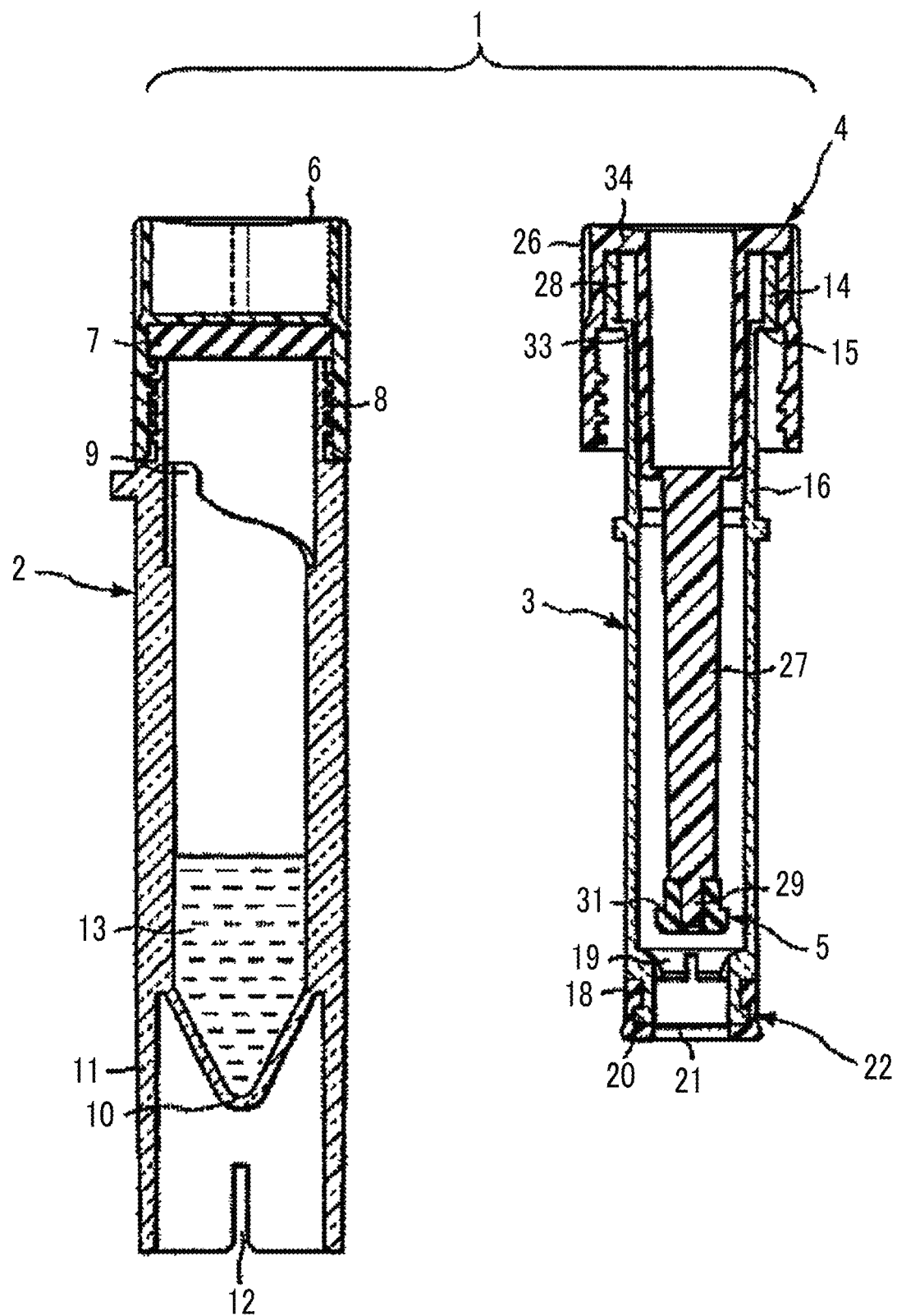
FIG. 1 illustrates an example of a configuration of a container for storing blood plasma components recovered from a diluted blood sample.

Hereinafter, embodiments of the present invention will be described.

A normal component homeostatically present in the blood refers to an external standard substance or an external standard.

A normal component not present in the blood refers to an internal standard substance or an internal standard.

In a medical institution or a test lab, the blood is collected from the vein of a patient or a subject to be tested for medical treatment or diagnosis of diseases, or health management. It is necessary to wait for a long period of time in order to know the result of the test, and there was a case where blood collection from the vein may be a burden depending on the child. In addition, including a movement for a test, half a day more is required, and there was a case where inconvenience occurred depending on a patient or a subject to be tested. In view of the above circumstance, it has been known that a patient or a subject to be tested performs self-blood collection to collect a small volume of blood at home, a test room, and the like, and stably stores and transports the blood.

As a method of collecting a small volume of blood, a method of performing blood analysis using a filter paper is disclosed in JP1998-104226A (JP-H10-104226A), and a method of using a porous material having a high level of blood retention property instead of a filter paper is disclosed in JP2001-330603A. In the above-described methods, aiming for extracting and measuring blood components absorbed in the material with a buffer solution and the like, sodium ions, chloride ions, calcium ions, protein, and the like which are homeostatically present in the blood are used as a reference substance in order to estimate a dilution ratio by a buffer solution used for a case of elution of blood. In the method of JP2001-330603A, there is a variation in a volume of blood collection, and in a case where a dilution ratio of the collected blood is high, there is a problem that analysis accuracy deteriorates, and thus the result varies, and there is a problem that because the blood is coagulated and solidified, the stability of the target component to be analyzed cannot be guaranteed. In addition, to a buffer solution for extracting the target component to be analyzed from a dried specimen, NaOH, NaCl, or HCl needs to be added in order to adjust the pH and stabilize the target component to be analyzed. Therefore, there is a problem that concentrations of sodium ions and chloride ions which are the most homeostatic components in the blood and have little difference between individuals, cannot be used as an external standard for correcting a concentration of a target component.

Meanwhile, JP2003-161729A discloses a method for diluting a small volume of the collected blood with a buffer solution containing an internal standard and quantitatively determining an amount of components present in the diluted blood plasma from a dilution factor of the internal standard substance. In JP2003-161729A, N-(2-hydroxy-3-sulfopropyl)-3,5-dimethoxyaniline sodium salt (HSDA) or acid blue 9 (brilliant blue FCF) is used as an internal standard substance. A method in which in a case of using HSDA, a dilution ratio is obtained by examining the absorbance of a coloring agent produced by the enzyme reaction using a second reagent, after dilution is disclosed, and a method in which in a case of using acid blue 9, a dilution factor is obtained from an absorbance of HEPES buffer solution, before and after addition of serum is disclosed. In addition, a buffering agent and a preservative are used for stably maintaining the blood. Such a formulation realized maintaining the stability of the components thereof by not coagulating the blood, but in a case where a volume of blood collection varies and a collection volume is small, there still were problems that a dilution ratio of an internal standard substance after dilution becomes small, and the reliability of test accuracy deteriorates as an amount of blood components itself decreased. In addition, in the method of diluting with a buffer solution, a biological component is stored in a buffer solution at physiological conditions of pH 7.4, and thus is excellent in stability during transportation, but because a specimen is added to a buffer solution to which an internal standard was added, a dilution ratio of the internal standard is small, and there is a problem that with addition of only a small amount of the specimen, a measurement error is likely to occur.

As described above, in a case of performing a blood test with a small volume of the blood, use of an external standard substance disclosed in JP2001-330603A and use of a buffer solution containing an internal standard substance disclosed in JP2003-161729A were not sufficient for ensuring test accuracy.

In sodium ions which are homeostatic substances in the blood, a distribution width of a normal value is 134 to 146 mmol/liter, and therefore it is necessary to more accurately calculate a dilution factor. A decrease of the accuracy of a dilution factor affects a bad influence on the test accuracy, and therefore a risk of deteriorating the reliability of a test increases. In addition, blood collection is an invasive action that damage the skin, and there is a desire for completing the action of blood collection fast depending on the person who performs the blood collection, and therefore volume of blood collection is not always in a constant volume and a variation occurs. Accordingly, in a case where a volume of blood collection is large or small, the accuracy of a dilution factor decreases as described above, and therefore visualizing a volume of blood collection and keeping the volume constant have been desired.

JP2001-330603A discloses the external standard, but does not disclose visualizing a volume of blood collection and keeping the volume constant. JP2003-161729A discloses the internal standard, but does not disclose a combination with the external standard. JP2003-161729A does not disclose the removal of substances having high homeostasis such as sodium and potassium which are preferable as an external standard substance, from a buffer solution used as a diluent solution, and does not disclose specific means for achieving the above. JP2001-330603A and JP2003-161729A do not disclose a means for quantitatively collecting a small volume of blood at high accuracy by self-blood collection.

According to a blood test kit and a blood analysis method of the present invention, even in a case where a volume of blood collection is not always a constant volume and a variation occurs, it is possible to confirm the volume of blood collection in a container in which blood is diluted and blood plasma is recovered, by which it is possible to perform analysis of a target component to be measured by obtaining dilution factor at high accuracy, compared to the methods disclosed in JP2001-330603A and JP2003-161729A. Furthermore, by using a method in combination, which is for obtaining a dilution factor using an internal standard, it is possible to further improve the accuracy. As described above, it is possible to perform measurement at high accuracy by analyzing a target component to be measured by obtaining a dilution factor in a state where a volume of blood collection is within a certain range and thus a variation occurs less. This is not known in the related art, and the fact that it is possible to perform blood analysis at high accuracy according to the configuration of the present invention is beyond the expectation.

According to the blood test kit and the blood analysis method of the present invention, in a case where a patient performs self-blood collection, even if volume of blood collection is not always in a constant volume and a variation occurs for example, it is possible to know a volume of blood collection from a container in which blood is diluted and blood plasma is separated, which enables a person who performs blood collection or an analyst to predict a result of a dilution factor within a narrow range. Therefore, it is possible to realize a high level of reproducibility with respect to a dilution ratio and to perform analysis of a target component to be measured at high accuracy. The collection of a small volume of blood using the blood test kit of the present invention is not limited by time and place, and can be applied to cases where there is no time to go to a medical institution, disaster, telemedicine, health management, and the like. Regarding a presymptomatic patient, a disease can be found at an early stage, and thus this blood collection contributes to save medical expenses. In addition, a large amount of a specimen can be efficiently measured with a commercially available biochemical/automated immunoassay analyzer. The measured test data is converted into electronic data and sent to a smartphone, and therefore can be used for a system for health management on a daily basis and early detection of diseases. Furthermore, according to the present invention, it is possible to perform various tests such as biochemical test (13 items), tumor markers, and hepatitis tests, using a small volume of blood (65 µl).

[1] Blood Test Kit

The blood test kit of the present invention is a blood test kit including a diluent solution for diluting components of a blood sample, and at least one transparent container for storing the components of the blood sample and the diluent solution, in which at least one constituent component included in the blood test kit is marked with a graduation for measuring the components of the blood sample and a liquid volume of the diluent solution.

(1) Diluent Solution for Diluting Components of Blood Sample

The blood test kit of the present invention is for performing analysis of a target component to be measured, in which a patient performs blood collection and transports the blood to a medical institution or a test institution, and there is a possibility that the blood is left alone for a long period of time from the blood collection to the analysis. During this time, it is preferable to prevent decomposition or denaturation of the target component in the diluent solution of blood. A pH of blood is generally maintained constant at a pH of about 7.30 to 7.40 for healthy subjects. Accordingly, in order to prevent decomposition or denaturation of the target component, the diluent solution preferably has pH 6.5 to pH 8.0, more preferably pH 7.0 to pH 7.5, and further preferably pH 7.3 to pH 7.4, and is preferably a buffer solution containing a buffering component for suppressing variation in pH.

As the type of the buffer solution, there are an acetate buffer solution (Na), a phosphate buffer solution (Na), a citrate buffer solution (Na), a borate buffer solution (Na), a tartrate buffer solution (Na), a Tris (tris(hydroxymethyl) aminoethane buffer solution (Cl), a HEPES ([2-[4-(2-hydroxyethyl)-1-piperazinyl]ethanesulfonic acid]) buffer solution, a phosphate buffered saline (Na), and the like. Among these, as a buffer solution around pH 7.0 to pH 8.0, a phosphate buffer solution, a Tris buffer solution, and a HEPES buffer solution are representative. However, the phosphate buffer solution contains a sodium salt of phosphoric acid. The Tris buffer solution has a dissociation pKa (Ka is an acid dissociation constant) of 8.08, and therefore these solutions are usually used in combination with hydrochloric acid for maintaining buffering ability around pH 7.0 to pH 8.0. A dissociation pKa of a sulfonic acid of HEPES is 7.55, but in order to adjust buffer solution at constant ionic strength, a mixture of sodium oxide and sodium chloride with HEPES is used. Therefore, these solutions are useful as a buffer solution having an action of maintaining pH constant but contain sodium ions or chloride ions which are substances preferably used as an external standard substance in the present invention, and therefore, application thereof to the present invention is not preferable. Therefore, the present inventors have conducted intensive studies and have found a new buffer solution not containing sodium ions and chloride ions.

The diluent solution which does not contain sodium ions and chloride ions and can be used in the present invention is preferably a diluent solution including at least an amino alcohol compound selected from the group consisting of 2-amino-2-methyl-1-propanol (AMP), 2-ethylaminoethanol, N-methyl-D-glucamine, diethanolamine, and triethanolamine, and at least one buffering agent selected from the group consisting of 2-[4-(2-hydroxyethyl)-1-piperazinyl]ethanesulfonic acid (pKa=7.55) also called HEPES which is a buffering agent having a pKa of around 7.4, N-tris(hydroxymethyl)methyl-2-aminoethanesulfonic acid also called TES (pKa=7.50), 3-morpholinopropanesulfonic acid also called MOPS (pKa=7.20), and N,N-bis(2-hydroxyethyl)-2-aminoethanesulfonic acid also called BES (pKa=7.15), which are Good's buffer solutions (Good's buffers). Among these, a combination of 2-amino-2-methyl-1-propanol (AMP) with HEPES, TES, MOPS, or BES is preferable, and a combination of 2-amino-2-methyl-1-propanol (AMP) with HEPES is most preferable.

For producing the buffer solution described above, an amino alcohol may be mixed with the Good's buffer solutions at a concentration ratio of 1:2 to 2:1, preferably 1:1.5 to 1.5:1, and more preferably 1:1. A concentration of the buffer solution is not limited, but a concentration of the amino alcohol or the Good's buffer solution is 0.1 to 1000 mM/L, preferably 1 to 500 mM/L, and more preferably 10 to 100 mM/L.

A chelating agent, a surfactant, an antibacterial agent, a preservative, a coenzyme, a saccharide, and the like may be contained in the buffer solution in order to keep a target component to be analyzed stable. Examples of the chelating agent include ethylenediaminetetraacetic acid (EDTA), citrate, oxalate, and the like. Examples of the surfactant include a cationic surfactant, an anionic surfactant, an amphoteric surfactant, and a nonionic surfactant. Examples of the preservative include sodium azide, antibiotics, and the like. Examples of the coenzyme include pyridoxal phosphate, magnesium, zinc, and the like. Examples of the saccharide of a red blood cell-stabilizing agent include mannitol, dextrose, oligosaccharide, and the like. Particularly, by adding the antibiotics, it is possible to suppress the growth of bacteria which are partially mixed from the surface of the finger at the time of collecting blood from the finger, suppress degradation of biological components by bacteria, and stabilize the biological components.

The components diluted with these buffer solutions do not interfere with the measurement even in a case of using various measuring methods by a biochemical/automated immunoassay analyzer. Furthermore, the components are preferable because blood cells are not hemolyzed, and biological components can be stored as stable as possible even at 37° C.

In a case where whole blood is used as a biological specimen, filtration of blood cell components in a diluted blood through a filter is required, and by setting osmotic pressure of the buffer solution equivalent to blood (285 mOsm/kg (mOsm/kg: an osmotic pressure that 1 kg of water of the solution has, and indicates millimoles of ions)) or more, it is possible to prevent hemolysis. The osmotic pressure can be adjusted to be isotonic by measurement of a target component, salts which do not affect a normal component homeostatically present in the blood, sugars, buffering agents, and the like.

A first example of the diluent solution for diluting the components of a blood sample is a diluent solution not containing a substance homeostatically present in the blood (hereinafter, will also be referred to as "homeostatic substance") used for obtaining a dilution factor. The phrase "does not contain" in the present specification means the solution "substantially does not contain". The phrase "substantially does not contain" means that the solution does not contain a homeostatic substance used for obtaining a dilution factor at all, or even if the homeostatic substance is contained, this means a case where an ultra-small volume of concentration is contained to the extent that does not affect measurement of a homeostatic substance in a diluent solution after diluting a blood sample. In a case where sodium ions or chloride ions are used as a homeostatic substance, a diluent solution which substantially does not contain sodium ions or chloride ions is used as a diluent solution.

In a case where the blood test kit of the present invention is a blood test kit for analyzing a concentration of a target component in a blood sample using normal components homeostatically present in the blood, a diluent solution is a diluent solution not containing above normal components.

A second example of a diluent solution for diluting components of a blood sample is a diluent solution containing an internal standard substance. The internal standard substance can be added to the diluent solution used for diluting a biological specimen so as to have a predetermined concentration. As the internal standard substance, it is possible to use a substance which is not contained in the blood sample at all, or is contained thereto but in an ultra-small amount. As the internal standard substance, it is preferable to use substances which do not interfere with the measurement of the target component in the blood sample, substances which do not decompose under the action of biological enzymes in the blood sample, substances which are stable in the diluent solution, substances which do not pass through a blood cell membrane and not contained in the blood cells, substances not adsorbed in a container storing the diluent solution, and substances which can be utilized by a detection system capable of measurement at high accuracy.

As the internal standard substance, a substance which is stable even if the substance is stored for a long period of time in a state of being added to a diluent solution which is a buffer solution, is preferable. Examples of the internal standard substance include glycerol 3-phosphate, Li, Rb, Cs, or Fr as alkali metal, and Sr, Ba, or Ra as alkaline earth metal. Among these, glycerol 3-phosphate or Li is preferable. These internal standard specimens can develop color by adding a second reagent at the time of measuring a concentration after blood dilution, and the concentration in the diluted blood can be obtained from color optical density. For example, measurement of lithium of an internal standard substance added to a buffer solution is carried out by the chelate colorimetric method (halogenated porphyrin chelating method: perfluoro-5,10,15,20-tetraphenyl-21H,23H-porphyrin) using an automatic biochemistry analyzer, and it is possible to easily measure a large number of specimens of a small amount.

In a case where the blood test kit of the present invention is a blood test kit for analyzing a concentration of the target component in the blood sample by using normal components not present in the blood, a diluent solution is diluent solution which contains the above normal components not present in the blood.

A third example of a diluent solution for diluting a blood sample is a diluent solution not containing normal components homeostatically present in the blood, which are used for obtaining a dilution factor, and containing an internal standard substance.

(2) Transparent Container for Storing Components of Blood Sample and Diluent Solution and Other Constituent Components A shape and a size of the transparent container for containing components of a blood sample and diluent solution are not particularly limited. The term "transparent" referred in the present invention may be transparent to the extent that the observer can confirm a volume of the solution therein, and is a concept including translucence and the like.

The material of the container is preferably a synthetic resin from the viewpoints of difficulty in breakage, sanitation, price, and the like. Examples thereof include polyethylene, polypropylene, polyvinyl chloride, polyvinylidene chloride, polystyrene, polyvinyl acetate, polyurethane, polyethylene terephthalate, polylactic acid, acrylonitrile butadiene styrene resin (ABS resin), acrylonitrile styrene resin (AS resin), acrylic resin (PMMA), polycarbonate, silicone resin, silicone rubber, and the like.

As the example of the blood test kit of the present invention, the kit can include a diluent solution for diluting components of a blood sample, a first storing instrument in which the diluent solution is stored, a separating instrument as a separation means for separating and recovering blood plasma from the blood sample diluted with the diluent solution, a holding instrument for holding the separating instrument, a second storing instrument for storing the recovered blood plasma, a sealing instrument for maintaining the stored blood plasma in the second storing instrument, a needle or a lancet for pricking the skin to allow blood to flow out of the skin, a strip of bandage or a sterile swab to be put on the wound (for example, nonwoven fabrics impregnated with isopropanol (70% by mass isopropanol and the like), ethanol, or the like), an instruction manual, and the like.

As the separation means for recovering blood plasma components from a diluted blood sample, an aspect of a separation membrane is preferable, and a filter having fine pores capable of separating blood cell components is more preferable. In the present invention, as the component of the blood sample, an embodiment of using blood plasma components separated from the blood sample by the separation means is preferable.

As the first storing instrument and the second storing instrument, one instrument may be used as both the first storing instrument and the second storing instrument, or an embodiment in which instruments are provided separately may be used. The first storing instrument and the second storing instrument is preferably made of a transparent material such that a patient or a measurer who performs measurement of a dilution factor or analysis of a target component to be analyzed can confirm a diluent solution in the storing instrument by which the blood is diluted.

As the holding instrument for holding the separating instrument, an aspect of a gasket is preferable. In addition, as the sealing instrument, in a case where the storing instrument is an instrument having a tubular shape, and the like, it is possible to use a cap capable of being used as a lid for the opening, a lid having a helical groove, a rubber closure, and the like.

With the above configuration, by imparting the function of separating blood plasma from blood cells to the container in which the blood is mixed with the diluent solution, immediately after diluting the blood with the diluent solution, it is possible to eliminate the influence on the stability of the blood components and the variation of the components due to hemolysis, and to impart the stability of the specimen after blood collection.

As a specific configuration example of the first storing instrument in which a diluent solution is stored, the separating instrument for separating and recovering blood plasma from a blood sample diluted with the diluent solution, the holding instrument for holding the separating instrument, the second storing instrument for storing the recovered blood plasma, and the sealing instrument for keeping the blood plasma in the second storing instrument, it is possible to use instruments described in FIG. 1 to FIG. 13 of JP3597827B, for example. FIG. 1 of JP3597827B is incorporated as FIG. 1 of the present application.

A blood separating instrument 1 includes a blood collection container 2 (first storing instrument in which a diluent solution is stored), a tubular body 3 capable of being to fit into the blood collection container 2 so as to be inserted (second storing instrument for storing recovered blood plasma), a cap piston 4 capable of being capped on the tubular body 3, and a sealing lid 5 (sealing instrument) provided at a lower end of the cap piston 4. Before use, an upper end opening portion of the blood collection container 2 is sealed by a cap 6 via a packing 7, as shown in FIG. 1. A container for storing a diluted blood sample of the present invention corresponds to a combination of the blood collection container 2 and the tubular body 3 in the configuration of FIG. 1. That is, the container for storing a diluted blood sample may be one or a combination of two or more thereof.

The blood collection container 2 is made of a transparent material and has a cylindrical shape. At the upper end portion thereof, a screw portion 8 is formed on the outer surface, and a locking portion 9 is protruded toward the inner surface. In addition, at a lower end portion of the blood collection container 2, a bottom portion 10 having an inverted conical shape is formed, and a cylindrical leg portion 11 is formed around the bottom portion 10. The leg portion 11 has the same outer diameter as a sample cup used at the time of an analytical test of blood, and at positions opposite to the lower end thereof, slit grooves 12 are preferably formed in a vertical direction, respectively. Furthermore, a predetermined volume, for example, 500 mm$^3$ of a diluent solution 13 may be put in the blood collection container 2 in advance, as shown in FIG. 1.

The tubular body 3 is made of a transparent material and has a cylindrical shape, and at an upper end portion thereof, an expanded diameter section 14 is formed. The expanded diameter section 14 is connected to a main body portion 16 via a thin portion 15. A reduced diameter section 18 is formed at the lower end portion of the tubular body 3, and a protruded locking portion 19 is formed on the inner surface of the reduced diameter section 18. Furthermore, at a lower end portion of the reduced diameter section 18, an outer flange portion 20 (holding instrument) is formed, a lower end opening portion of the outer flange portion 20 is covered with a filtration membrane 21 (separating instrument), and the filtration membrane 21 allows blood plasma in the blood to pass through and prevents passage of the blood cells.

A cover 22 made of silicone rubber is attached to the outer periphery of the reduced diameter section 18 (FIG. 1).

The cap piston 4 is constituted by a substantially cylindrical knob portion 26 and a mandrel portion 27 concentric with the knob portion 26 and extending downward. At an inner upper end portion of the knob portion 26, a cylindrical space 28 into which the expanded diameter section 14 of the tubular body 3 is capable of being fitted to be inserted is formed, and the knob portion is threaded in a lower portion into which a screw can screw. The mandrel portion 27 has a lower end portion 29 formed in a pin shape, and a sealing lid 5 is detachably provided on the lower end portion 29 (refer to FIG. 1). The sealing lid 5 is made of silicone rubber.

A method for separating blood by the instruments described above is described in detail in paragraphs 0023 to 0026 and FIG. 12 and FIG. 13 of JP3597827B, the contents of which are incorporated in the present specification.

(3) Graduation

In the present invention, at least one constituent component included in the blood test kit is marked with a graduation for measuring the components of the blood sample and a liquid volume of the diluent solution. With the above graduation, a person who performs blood collection or a tester can confirm that a volume of blood collection is equal to or more than a certain volume. The number of graduations may be one, or there may be a plurality of, for example, 2 or more thereof. Examples thereof can include a case where a single graduation indicating a certain volume required at the minimum is marked, a case where two graduations indicating a lower limit volume and an upper limit volume is marked, a case where three graduations indicating a lower limit volume and an upper limit volume, and an intermediate standard volume therebetween is marked, and the like. In addition, it is possible to impart the meaning for the graduations by putting different colors on the graduations. In addition, the graduation may include at least a graduation for measuring a liquid volume of the diluent solution not containing the components of a blood sample. By showing a desired value of a liquid volume with the graduation at the time of weighing of the diluent solution and at the time of blood collection, it is possible to design a blood volume and a diluent solution volume appropriate for designing components of the diluent solution, with a high level of reproducibility.

As long as a person who performs blood collection or a tester can confirm that a volume of blood collection is in a certain volume or more, the graduation can be marked on an arbitrary constituent component of the blood test kit, but preferably, the graduation can be marked on at least one transparent container for storing the components of a blood sample and the diluent solution. In a case where the transparent container is marked with the graduation, it is possible to mark the graduation in a manner of interposing a liquid, by which confirming of a liquid volume becomes easy, which is preferable.

Examples of the above-mentioned constituent component in a case where the transparent container for storing the components of a blood sample and the diluent solution is marked with the graduation include a mandrel portion of a sealing cap for preventing back flow.

A configuration in which the blood test kit contains a bottle (container) in which a diluent solution for diluting blood is stored, a separation membrane for separating blood cell components from blood plasma components of blood, a gasket for holding the separation membrane, and cylinder (container) in which blood plasma components after separation is stored, will be described. In this configuration, in a state of no blood collection, the cylinder is inserted into the bottle and then separated, graduations capable of measuring an increase in a liquid volume from a liquid surface in a state where a mandrel portion of a sealing cap for preventing back flow of the separated solution is inserted, are marked thereto, and therefore it is possible to confirm a volume of the blood plasma components of the volume of blood collection. If both the bottle and the cylinder are transparent, the graduations can be marked on either side. In addition, when the cylinder is inserted into the bottle, the cylinder is pushed until the cylinder comes into contacts with the bottom of the bottle, but a reference line is marked on both the bottle and the cylinder, and in a case where the cylinder is thorough sufficiently pushed in such that positions of each reference line match, a volume of the blood plasma components being not accurately measured due to insufficient pushing can be prevented.

Regarding an inner diameter of the transparent container for storing the components of a blood sample and the diluent solution, it is preferable that a liquid volume of the diluted blood plasma separated after dilution matches a position of the graduation. An inner diameter of the container in the case is preferably 5 mm or less, and more preferably about 3 mm in order to increase the detection sensitivity. For example, in a case where the diameter is 3 mm theoretically, if a position of the graduation ±0.5 mm can be visually confirmed, a difference of about ±14 µL can be detected, and in a case of 5 mm, a difference of about ±40 µL can be detected.

Furthermore, if a diameter of the mandrel portion for pushing a valve for preventing back flow after blood plasma separation is 2 mm, a detection area of a liquid volume is 5 mm in width, and an inner wall diameter of the cylinder in that area is 3 mm, even if the position accuracy of the graduation is ±1.0 mm, it is possible to detect a difference of a liquid volume at an accuracy of about ±12 µL due to the volume reduction effect inside the cylinder by the mandrel portion. In such a case, by marking three or more graduation lines at a width of a target liquid volume ±1.0 mm, a degree of insufficient liquid volume can be reduced to 12 µL or less. This is shown in FIG. 2.

Figure 2:
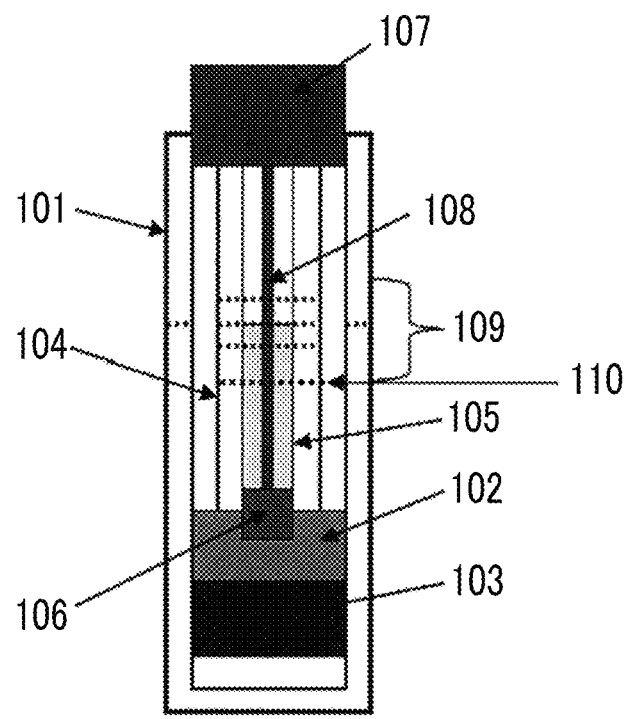
FIG. 2 illustrates a schematic diagram of graduations of a bottle and a cylinder at the time of blood plasma separation and sealing.

FIG. 2 illustrates a schematic diagram of the graduations of the bottle and the cylinder at the time of blood plasma separation and sealing. By filtering the blood placed at a lower portion of a transparent bottle 101 with a blood plasma separation membrane in a gasket 102 including the blood plasma separation membrane, blood cells 103 mainly present at the lower portion of the transparent bottle 101, and blood plasma 105 is mainly present in the inside of a transparent cylinder 104 attached to the inside of the transparent bottle. After separating blood cells from blood plasma, a mandrel portion 108 having a back flow prevention valve 106 at one distal end thereof and having a sealing cap 107 at the other distal end thereof, is inserted into the transparent cylinder 104, and the back flow prevention valve 106 is mounted in a gasket 102 including the blood plasma separation membrane. As a result, the blood plasma 105 in the transparent cylinder 104 does not flow back to the place of which the blood cells are present at the lower portion of the transparent bottle. In FIG. 2, one graduation 109 is marked to the transparent bottle and three graduations are marked to the transparent cylinder. The graduation of the transparent bottle and the graduations in the middle of the transparent cylinder indicate a standard volume. The graduations below the transparent cylinder and the graduations on the upper side thereof indicate a lower limit volume and an upper limit volume, respectively. In addition, a graduation 110 of the diluent solution indicate a graduation in a case of only a diluent solution in which plasma is not diluted. The increased volume from these graduations corresponds to a volume of the blood plasma components before dilution.

In a case where at least one transparent container for storing a mixed solution of the components of a blood sample and the diluent solution is marked with the graduation, the transparent container, the transparent container has a portion of which an interior cross-sectional area is smaller than that of other portions, and it is preferable that the portion of which the interior cross-sectional area is smaller than that of other portions is marked with the graduation. It is further preferable that a portion of the transparent container of which an interior cross-sectional area is smallest is marked with the graduation. The internal cross-sectional area means a cross-sectional area in a case where the space inside the transparent container is cut along one horizontal plane. Since the portion marked with the graduation is a portion for accurately measuring a liquid volume, measurement at high accuracy becomes possible by marking the graduation on the portion having a small interior cross-sectional area as described above.

In a case where the container has a cylindrical shape, it is possible to provide a portion having a small interior cross-sectional area by providing a portion having a small inner diameter. For example, a part of the cylinder is constricted thinly, and by marking the graduation on the constricted portion, a volume of the blood plasma components can be accurately measured. However, in a case of inserting the mandrel portion of the sealing cap for preventing back flow of the separated solution, the constricted portion of the cylinder has a thickness enough to allow the mandrel portion to be inserted, and in consideration of the capacity of the mandrel portion, it is preferable that the graduation marked on the constricted portion so that a volume of the blood plasma components can be accurately measured.

Regarding the portion of which an interior cross-sectional area is smaller than that of other portions, in the case where an inner diameter is narrow for example, it is preferable to mark on a portion which becomes a half of the inner diameter of the narrowed portion.

FIG. 3A to FIG. 4B illustrate an aspect in which a part of the cylinder is constricted thinly. In FIG. 3A to FIG. 4B, a graduation 202 is marked on a narrow portion of an upper portion of a cylinder 201. In addition, a graduation 206 for the dilution solution is marked.

Figure 3A:
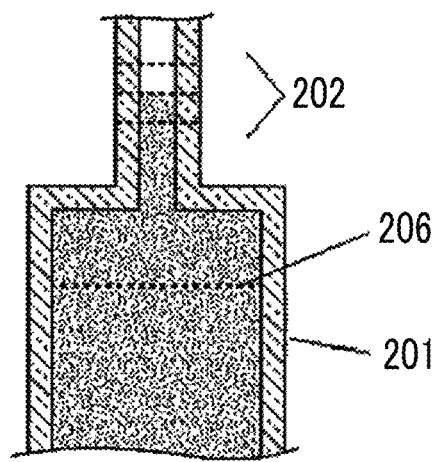
FIGS. 3A and 3B illustrate an example of a shape of a container and positions of graduations.
Figure 3B:
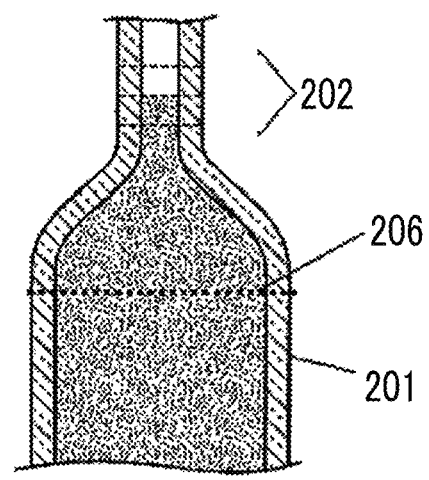
Figure 4A:
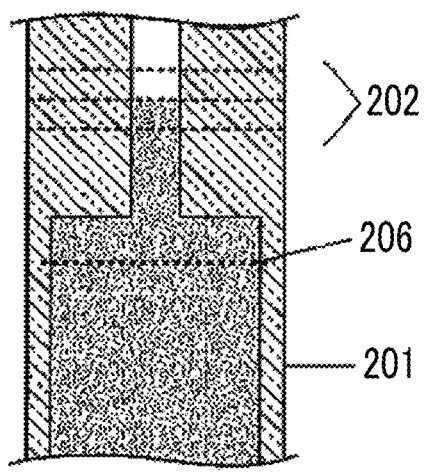
FIGS. 4A and 4B illustrate an example of a shape of the container and positions of the graduations.
Figure 4B:
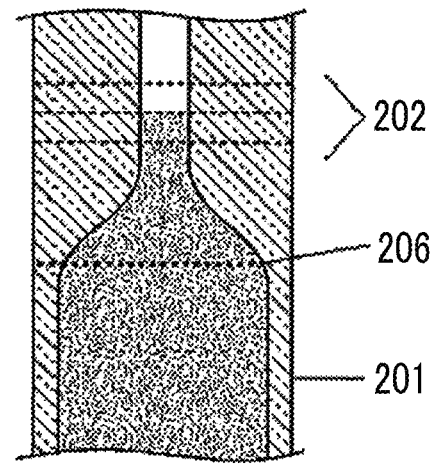

FIGS. 3A and 3B illustrate an aspect in which a thickness of the container has a portion smaller than the other portions (the thickness of the outer wall of the container is the same), FIG. 3A illustrates an aspect in which the thickness of the container changes at a certain portion, and FIG. 3B illustrates an aspect in which the thickness of the container changes continuously. FIGS. 4A and 4B illustrate an aspect in which an inner diameter of the container has a portion smaller than the other portions (the thickness of the container is the same), FIG. 4A illustrates an aspect in which the inner diameter of the container changes at a certain portion, and FIG. 4B illustrates an aspect in which the inner diameter of the container changes continuously.

Figure 5:
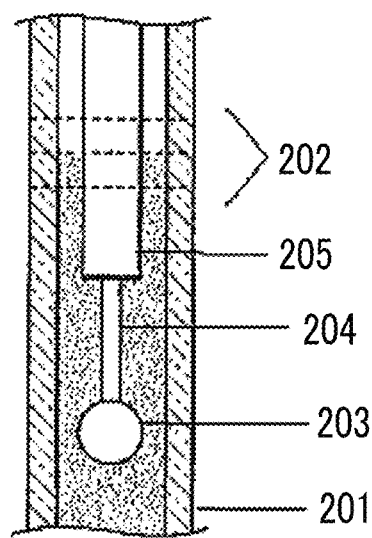
FIG. 5 illustrates an example of a shape of the container and positions of the graduations.

In addition, as the configuration illustrated in FIG. 2, in a case of inserting the mandrel portion having the back flow prevention valve, it is possible to provide a portion having a small interior cross-sectional area by providing a thick portion in the thickness of the mandrel portion (FIG. 5). In FIG. 5, a graduation 202 is marked on an upper portion of the cylinder 201. In addition, the graduation 206 for the dilution solution is marked. The mandrel portion having a back flow prevention valve 203 has a narrow portion 204 and a thick portion 205, and the graduation is marked on a position corresponding to the thick portion 205.

(4) Form of Providing Blood Test Kit

The number of various components contained in the blood test kit of the present invention is not particularly limited, and each component may be one, or there may be a plurality of, for example, 2 or more of the components.

The blood test kit of the present invention can be provided in the form of being stored in a storage container for storing the diluent solution for dilution the components of a blood sample, at least one transparent container for storing the components of a blood sample and the diluent solution, and another constituent component if necessary.

[2] Blood Analysis Method

A blood analysis method of the present invention is a blood analysis method which uses a blood test kit including a diluent solution for diluting components of a blood sample and at least one transparent container for storing the components of the blood sample and the diluent solution, and is a method including a step of selecting a specimen containing the blood sample components of a predetermined amount or more which have been determined in advance, as an analysis target specimen so as to exclude a specimen containing the blood sample components of less than the predetermined amount from the analysis target specimen, and a step of analyzing the blood by using the specimen containing the blood sample components which have been selected from the above step.

The configuration of the blood test kit used in the blood analysis method of the present invention the same as described in [1] of the present specification, but a graduation for measuring the components of a blood sample and a liquid volume of the diluent solution may be marked on at least one constituent component contained in the blood test kit, or may not be marked. Preferably, it is possible to use the blood test kit in which the graduation is marked on at least one constituent component contained in the blood test kit. Using the above graduations enables easy performance of selecting a specimen containing the blood sample components of a predetermined amount or more which have been determined in advance, as an analysis target specimen so as to exclude a specimen containing the blood sample components of less than the predetermined amount from the analysis target specimen.

The blood analysis method of the present invention may be carried out by self-blood collection in which a subject collects the blood by himself, or may be carried out by general blood collection in which a qualified person such as a doctor collects the blood using a syringe.

In the present invention, a biological specimen which is an analysis target is blood, and the blood is a concept including serum or blood plasma. Preferably, it is possible to use blood plasma or serum obtained by collecting a small volume of blood from the subject to be tested, diluting the blood with a diluent solution, and then separating blood cells through a filter or by centrifugation. The components of a blood sample are preferably blood plasma components separated from the blood sample by a separation means.

The origin of a blood sample is not limited to humans, and may be an animal other than humans (mammals, birds, fish, and the like), and the like. Examples of the animal other than humans include horses, cows, pigs, sheep, goats, dogs, cats, mice, bears, pandas, and the like. The origin of a biological specimen is preferably humans.

As a preferred embodiment, a patient himself pricks a fingertip and the like using a blade-attached instrument such as a lancet and then collects the blood flowing out of the skin. It is preferable that the blood is collected in a manner of reducing the invasiveness so to alleviate the burden on a patient, and when collecting the blood, it is desirable to be able to collect the blood with little pain or painlessly. In this case, it is desired that a depth and a size of the wound are small, and therefore, a volume of blood collected from a patient, which is used for the analysis method of the present invention is preferably 100 µl or less, and it is more preferable to perform the analysis by using blood of 10 µl or more and 70 µl or less. Even in such a region where a small volume of blood is collected, in the present invention, a person who performs the blood collection can recognize that the volume of blood collection is small, and can supplement and compensate the volume. Even if a volume of blood collection is small, it is possible to recognize that a volume of blood collection is insufficient from a container in which blood is diluted and blood plasma is separated, which enables a person who performs blood collection or an analyst to predict a result of a dilution factor within a narrow range. Therefore, it is possible to provide a method for measuring an analysis target at high measurement accuracy.

In a first embodiment of the blood analysis method of the present invention, a component homeostatically contained in a blood sample is used as a normal component. Specific examples thereof include sodium ions ($Na^+$), chloride ions ($Cl^-$), potassium ions ($K^+$), magnesium ions ($Mg^{2+}$), calcium ions ($Ca^{2+}$), total protein ("TP"), albumins, and the like. As a concentration of these normal components contained in a blood sample, a concentration of Na is 134 to 146 mmol/litre (average value: 142 mmol/litre), a concentration of Cl is 97 to 107 mmol/litre (average value: 102 mmol/litre), a concentration of K is 3.2 to 4.8 mmol/litre (average value: 4.0 mmol/litre), a concentration of Mg is 0.75 to 1.0 mmol/litre (average value: 0.9 mmol/litre), a concentration of Ca is 4.2 to 5.1 mmol/litre (average value: 4.65 mmol/litre), a concentration of total protein is 6.7 to 8.3 g/100 mL (average value: 7.5 g/100 mL), a concentration of albumins is 4.1 to 5.1 g/100 mL (average value: 4.6 g/100 mL). Among these, when the blood components of a small amount are diluted with a high dilution ratio of 5 or larger, in order to detect the homeostatic normal components therein at sufficiently high accuracy, it is preferable to measure a standard substance present in the blood at a high concentration. In addition, it is considered that even in a case in which unintended components other than blood are mixed in a diluent solution, the standard substance present in the blood at a high concentration is highly resistant to the influence of contamination and can suppress a deterioration of the test accuracy. As such normal components, sodium ions or chloride ions is preferable, and among the normal components homeostatically present in the blood, sodium ions which are present in the blood at a highest amount are most preferable. Na ions have a standard value (normal value) of 142 mmol/liter, accounting for 90% or more of total cations in the blood plasma.

In the blood analysis method of the first embodiment described above, blood plasma is recovered from a blood sample using a blood test kit including a diluent solution not containing the normal components homeostatically present in the blood, the recovered blood plasma is diluted with the diluent solution, and using the normal components homeostatically present in the blood, a dilution factor of the diluted blood plasma is determined, and therefore it is possible to analyze a concentration of a target component in the blood sample.

A concentration of sodium ions and a concentration of chloride ions can be measured by, for example, the flame photometric method, the atomic absorption method, the glass-electrode method, the titration method, the ion selective electrode method, the enzyme activity method, and the like.

In the present invention, a specimen obtained by collecting a small volume of blood from a finger and diluting the blood with a diluent solution is only about 150 μl, and it is preferable that measurement of an external standard substance can be performed with a small volume of several μl because 10 or more items of biochemical components and immunological test items are measured. In addition, since it is necessary to analyze a large number of specimens, it is preferable that application thereof to a commercially available biochemical/automated immunoassay analyzer is possible.

In the present invention, a preferred standard substance is sodium ions, and a dilution factor (Y/X) of a blood sample is calculated from a measurement value (concentration X) of sodium ions in a diluent solution after diluting the blood, and a known concentration value (concentration Y; 142 mmol/liter) of sodium ions, which is a normal component of the blood sample. By multiplying this dilution factor by a measurement value (concentration Z) of a target component to be analyzed in the diluted blood sample, it is possible to obtain a concentration [Z×(Y/X)] of the target component to be analyzed actually contained in blood plasma of the blood sample.

In addition, in order to verify whether diluting the blood, and separating and recovering the blood plasma are normally performed, it is preferable that by using two or more different normal components which are homeostatically present in the blood plasma, dilution factors are separately obtained for each, and then it is confirmed whether values thereof match. The term "match" means, with respect to two measurement values (a, b), a ratio of their differences to their average values, that is, $|a-b|/\{(a+b)/2\}\times 100$ is 20% or smaller, preferably 10% or smaller, and more preferably 5% or smaller. As a preferred embodiment, regarding the concentration analysis of a target component in the blood sample, which is performed using a dilution factor obtained from a measurement value of a concentration of sodium ions in a diluent solution and a known concentration value (142 mmol/liter) of sodium ions in the blood plasma, by confirming that a dilution factor obtained from a normal component which is homeostatically present in the blood plasma, other than sodium ions matches a dilution factor obtained from a concentration of sodium ions, it is possible to verify that analysis of the components contained in the blood plasma of the blood sample is normally performed. The normal component used for the analysis of a concentration of the target component is preferably selected from sodium ions or chloride ions, and the normal component used for verifying the analysis is preferably selected from total protein or albumins, and more preferably selected from total protein. Examples of a method for measuring total protein include the biuret method, the ultraviolet absorption method, the Bradford method, the Lowry method, the bicinchoninic acid (BCA) method, the fluorescence method, and the like, and it is possible to select a method to be used appropriately depending on characteristics, sensitivity, specimen amount, and the like of a measurement specimen.

In a second embodiment of the blood analysis method of the present invention, a dilution concentration is determined by using a normal component not present in the blood. In this case, blood plasma is recovered from the blood sample using a blood test kit including a diluent solution containing a normal component not present in the blood, the recovered blood plasma is diluted with the diluent solution, and a dilution factor of the diluted blood plasma is determined using the normal component not present in the blood, and therefore a concentration of a target component in the blood sample can be analyzed.

It is known that sodium in the blood has extremely a high level of homeostasis and variations among individuals are small. In addition, a concentration of a median value thereof is 142 mmol/L, which is high as a biological concentration, and therefore a concentration thereof can be measured at high accuracy even being diluted with a diluent solution. Furthermore, an internal standard in the diluent solution for dilution can be set to a high concentration, and therefore a concentration can be measured at high accuracy.

In a third embodiment of the blood analysis method of the present invention, blood plasma is recovered from the blood sample using a blood test kit including a diluent solution containing a normal component not present in the blood, the recovered blood plasma is diluted with the diluent solution, and a dilution factor of the diluted blood plasma is determined using the above-described normal component homeostatically present in the blood and the normal component not present in the blood, and therefore a concentration of a target component in the blood sample can be analyzed. By combining the measurement absorbance of the internal standard solution with the measurement absorbance of the external standard of the component having a high level of homeostasis of the specimen as described above, it is possible to complement the defects of the above two quantitative methods as a measurement method having high measurement accuracy, and therefore the method can be used as a quantitative method for diluted components, which has high reliability.

It is preferable that a dilution ratio of the components of a blood sample is calculated by any one of Formulas 1 to 4, and a concentration of the target component to be analyzed in the diluent solution is multiplied by the above dilution ratio, and therefore a concentration of target component in the components of a blood sample is analyzed.

$$X=(A+C)/(B+D) \qquad \text{Formula 1}$$

$$X=\{(A^2+C^2)^{1/2}\}/\{(B^2+D^2)^{1/2}\} \qquad \text{Formula 2}$$

$$X=a\times(B+D)\pm b \qquad \text{Formula 3}$$

(a and b are coefficients, and a standard curve represented by Formula 3 is prepared in advance by acquiring data of (B+D) and a dilution factor)

$$X=A/B' \qquad \text{Formula 4}$$

$$(B'=(A\times D)/C)$$

In the above formulas, A, B, C, B', and X are defined as follows.
A: Measurement absorbance of the diluent solution containing an internal standard substance
B: Absorbance obtained by subtracting an absorbance of the diluent solution by which the components of the blood sample is diluted from A
C: Measured absorbance in which a concentration of sodium ions, as a homeostatic substance, is 142 mmol/L
D: Absorbance of sodium ions in the diluent solution by which the components of the blood sample is diluted
B': Correction value of an absorbance of a normal component not present in the blood in diluted blood plasma obtained by a dilution factor calculated from an absorbance of blood plasma sodium
X: Dilution factor of blood plasma As another calculation method for a case of obtaining a dilution ratio, an aspect in which a dilution ratio is calculated by Formula 5 using the root-mean-square method, a concentration of a target component to be analyzed in a diluent solution is multiplied by the dilution ratio calculated by Formula 5, and therefore a concentration of a target component in the components of a blood sample is analyzed, is preferable.

$$X=[\{(A/B)^2+(C/D)^2\}/2]^{1/2} \qquad \text{Formula 5}$$

In a case of testing a specific organ or a specific disease such as liver function, renal function, metabolism, and the like as a blood test, analysis of a plurality of target components to be measured is generally performed at the same time in order to perform a prediction and the like of a state of the organ, a lifestyle habit, and the like by obtaining information of the plurality of target components to be measured which are specific to the organ or the disease. For example, in order to test the state of a liver, generally, a concentration of various components in the blood such as ALT (alanine transaminase), AST (aspartate aminotransferase), γ-GTP (γ-glutamyl transpeptidase), ALP (alkaline phosphatase), total bilirubin, total protein, and albumins is measured. As above, in order to measure the plurality of target components from one blood sample, a certain volume of diluted blood is required in a case of considering a possibility of measuring again. Accordingly, regarding a diluent solution for diluting the collected blood, it is important that a certain volume thereof is secured. In a case of considering blood collection in which the invasiveness is reduced a little, an aspect in which a volume of blood collection is 100 μl or less is preferable, and in this case, a dilution factor of blood plasma which is the component of a blood sample 7 or more.

The present invention relates to the blood test kit for performing a test in which a patient performs blood collection and transports the collected blood to a medical institution or a test institution, and the blood analysis method using the blood test kit. Accordingly, from the blood collection to the test, there is a possibility that the blood is left alone for a long period of time in a diluted state. During the time, for example, red blood cells are hemolyzed, which leads to the release of substances, enzymes, and the like which are present at high concentration in the blood cells into the blood plasma or serum, and therefore a test result is affected thereby. Furthermore, in a case of measuring a target component to be analyzed by using tone, there is a possibility that hemoglobin affects the test. Therefore, it is necessary to prevent hemolysis, blood coagulation, and the like during transportation, and in the present invention, it is preferable to include a step of separating blood cells from blood after diluting the blood collected by the patient with a diluent solution.

A method for separating blood cells from blood and recovering blood plasma is not particularly limited. The separation of blood plasma after blood collection is preferably carried out immediately after diluting the blood with a diluent solution. A method in which blood is collected with a blood collection tube container containing an anticoagulant, and then centrifuged to separate the blood into blood cells and blood plasma components, and transported in a separate state, or pressure is applied on the blood components so that the components pass through a separation membrane such as filtration membrane, the blood components are trapped with the separation membrane, and therefore the blood components are separated from the blood, and the like are used. In this case, it is preferable to use an anticoagulant. In addition, in order to ensure the accuracy of measurement, it is preferable to physically separate the blood plasma from the solution portion of the blood excluding blood cell components. In this case, specifically, it is possible to use a biological specimen-separation instrument having a backflow prevention means described in JP2003-270239A, and the like.

In the present invention, analyzing of a concentration of a target component in a blood sample includes determining a concentration of a target component (that is, quantitatively determining a target component), determining whether a concentration of a target component is equal to or higher than a predetermined reference value or equal to or lower than a predetermined reference value, performing qualitative analysis for detecting that a certain amount of concentration is contained, and the like, and an embodiment of analysis is not particularly limited.

The target component to be analyzed is not limited, and any substance contained in a biological specimen is a target. Examples thereof include biochemical test items in blood used for clinical diagnosis, markers of various diseases such as tumor markers and hepatitis markers, and the like, and include proteins, sugars, lipids, low molecular weight compounds, and the like. In addition, not only a concentration of a substance is measured, but also an activity of a substance having an activity such as an enzyme is targeted. Measurement of each target component can be carried out by a known method.

An example of the blood analysis method of the present invention will be described below.

A blood specimen of a small volume of 65 μL was added to 280 μL of a diluent solution added with an internal standard and mixed, the blood cells were filtered through a filter, and using the diluted blood plasma as a specimen, each concentration of the internal standard, the external standard, and the biological component was measured using the automatic biochemistry analyzer.

According to one embodiment of the present invention, the method is a method in which, with respect to a large number of specimens, quantitation and enzyme activity of diluted blood plasma biological specimen components of unknown concentration in the collected blood are efficiently analyzed by using a commercially available biochemical/automated immunoassay analyzer. An external standard substance that uses plasma sodium or the like maintaining a certain concentration in a biological specimen, or lithium as a component that is not contained in or almost not contained in the blood plasma and as an internal standard substance which does not pass through the blood cell membrane are prepared, and are added to a buffer solution. Generally, in a case where an organic compound is used as an internal standard, depending on the type of the organic compound, there is a case in which the compound is influenced by the storage stability due to the action of the biological enzyme, and therefore it is necessary to confirm the stability. In a case where this lithium is used as an internal standard substance, the substance is stable in a diluent solution for a long period of time and can be easily quantitatively determined. In addition, sodium which is an external standard of a measurement specimen is an element and thus is stable.

As a measurement method in which plasma sodium diluted with a diluent solution is used as an external standard, there are the flame photometer, the atomic absorption method, and the ion selective electrode method. In the present invention, a blood plasma specimen obtained by collecting a small volume of blood from the finger and heel, diluting the blood with a diluent solution, and separating blood plasma and blood cell, is only about 300 µL, and it is necessary that measurement of an external standard sodium is performed with a small volume of several µl because 10 or more items of biochemical components and immunological test items are measured. In addition, since it is necessary to analyze a large number of specimens, it is necessary that application thereof to a commercially available biochemical/automated immunoassay analyzer is possible.

In the present invention, in a case of performing sodium measurement, it is preferable to use an enzymatic assay that can measure, with several µL, a specimen of very low sodium concentration (24 mmol/L or less) diluted with a diluent solution by utilizing that the enzyme activity of the enzyme galactosidase is activated by sodium ions. This method can be applied to a biochemical/automated immunoassay analyzer, and the method is particularly preferable because the method is highly efficient and economical for not required of another measuring instrument for sodium measurement.

Measurement of the lithium internal standard substance added to the diluent solution was carried out by the chelate colorimetric method (halogenated porphyrin chelating method: perfluoro-5,10,15,20-tetraphenyl-21H,23H-porphyrin) using an automatic biochemistry analyzer, and it is possible to easily measure a large number of specimens of a small amount.

The concentrations of sodium and lithium are measured in order to obtain a dilution ratio of blood plasma in the blood, and therefore, it is preferable that the diluent solution does not contain substances similar to these components or similar alkali metals, and it is preferable that pH can be adjusted to around pH7 to pH 7.4 which is a pH of blood plasma. Therefore, as an alkaline compound that does not contain alkali metals (such as NaOH), it is preferable to use an amino alcohol compound such as 2-amino-2-methyl-1-propanol, 2-ethylaminoethanol, N-methyl-D-glucamine, diethanolamine, and triethanolamine. In order to adjust pH of a diluent solution containing these alkaline compounds to around pH 7.4, it is preferable to use HEPES 2-[4-(2-hydroxyethyl-1-piperazinyl]ethanesulfonic acid) which is a buffering agent having a pKa of around pH 7.4, TES N-tris(hydroxymethyl)methyl-2-aminoethanesulfonic acid), MOPS 3-morpholinopropanesulfonic acid, and BES (N,N-bis(2-hydroxyethyl)-2-aminoethanesulfonic acid, which are the Good's buffer solutions having excellent performance for biochemistry, as an acid, in the diluent solution.

These diluent solutions do not contain alkali metals and alkaline earth metals such as sodium of an external standard and lithium of an internal standard, and do not interfere with a measuring system of sodium and lithium which are measurement targets, and therefore it is preferable that the diluent solutions are used as a diluent solution of the present invention. In addition, components diluted with these diluent solutions are not interfered even by various measuring methods using the biochemical/automated immunoassay analyzer, and blood cells are not hemolyzed and biological components can be stored stably even at 37° C., and therefore the diluent solutions are a preferred aspect as a diluent solution.

In order to measure biological components in the blood plasma diluted with the diluent solution, it is preferable that components in the diluent solution do not denature biological components in the blood plasma, or have substantially no influence on the stability. As an example of this, a diluent solution which has a buffering performance and in which 2-amino-2-methyl-1-propanol (AMP) is mixed with HEPES to adjust the pH to 7.4 does not denature biological components, and even in a case where the blood plasma components are diluted, each component is stable, and therefore the diluent solution is a buffer solution which does not interfere with measurement reagents of these biological components.

The embodiment in which the collected blood sample is diluted with the diluent solution, and then blood cell components in the blood are separated through a filter, is a preferred embodiment of the present invention, and by setting osmotic pressure of the diluent solution equivalent to (285 mOsm/kg (mOsm/kg: osmotic pressure that 1 kg of water of the solution has, and indicates millimoles of ions)) or higher than that of the blood, it is possible to prevent hemolysis. Furthermore, the embodiment is an embodiment in which in order to stabilize the blood cell membrane and the enzyme, adding mannitol or pyridoxal phosphate to the diluent solution is also preferable. In addition, the embodiment is an embodiment in which in order to suppress the decomposition of blood components due to the growth of bacteria partially mixed from the surface of the finger at the time of blood collection from the finger, adding 3 and 4 types of antibiotics to stabilize the decomposition of the biological components by bacteria is also preferable.

The measurement of a small amount of sodium in the diluted blood plasma is preferably performed using the enzymatic assay by utilizing that β-galactosidase is activated by sodium, which is that a concentration of sodium of the specimen diluted with the diluent solution and galactosidase are in a proportional relationship.

The present invention will be described by the following examples, but the present invention is not limited by the description of examples.

EXAMPLE

Example 1

Blood collection, blood plasma separation, and blood analysis were performed using DEMECAL (registered trademark) blood test kit (Leisure, Inc.), except for the cylinder and the spongy-like tip for collecting blood. The comparison was performed between a case where a graduation used as a measure of a liquid volume after separation of the blood plasma was marked on the cylinder (the present invention), and a case of not marking the graduation (comparative example).

Cylinder Marked with Graduation

Specification 1: A thickness of an inner wall and a width of the graduation were adjusted so that variations in a volume of separated blood plasma can be detected at 30 µl difference.

Specification 2: A thickness of an inner wall was changed from the cylinder of Specification 1 and was set such that a cross-sectional area of a portion marked with the graduation was reduced, and a width of the graduation was adjusted so that variations in a volume of separated blood plasma can be detected at 15 µl difference.

In a case where the graduation was marked and then the blood plasma separation was performed, when the cylinder was pushed down to the end and the diluted blood plasma was extracted in the maximum amount, it could be confirmed that a volume of blood collection was not insufficient. In a case of recognizing that the volume of blood collection is insufficient, the blood was collected again. A volume of the diluent solution set to be marked with the graduation was 300 µL and a volume of blood collection was targeted to be 65 µL.

After informed consent was obtained from volunteer patients, about 10 mL of blood collected by a syringe from the vein was obtained in a blood collection tube. Ten cylinders with no graduation, to which 300 µl of the diluent solution was added, and ten cylinders having the graduation were prepared (Specification 1 and Specification 2), respectively. Thereafter, about 65 µl of blood was collected with the sponge-like tip, the collected blood was mixed with the diluent solution of each cylinder so as to be diluted, the blood cells were separated from the mixed solution using a filter, and therefore the diluent solution of the blood plasma was collected. Information on an approximate amount of the diluted blood plasma was obtained from the cylinder having the graduation. The accuracy of repeatability with respect to measurement values was obtained by repeating the experiment ten times. A dilution ratio was determined according to the following method.

(Method 1)

In a case where the cylinder with no graduation was used, a dilution factor was calculated as 300 µl of the diluent solution by assuming that a blood volume was 65 µl and a hematocrit value (numerical value showing a ratio of the volume of the blood cells in the blood) was constant at 40%. In a case where the cylinder having the graduation was used, a volume of blood plasma was presumed from the graduation, and thereby a dilution factor was obtained using that value.

The components of the diluent solution used in the above experiment are described below. As a diluent solution, a diluent solution disclosed in JP2001-330603A was used except that the solution was designed while noting that a substance containing Na and containing impurities was not used. As osmotic pressure, a value measured by using OSMOATAT OM-6040 (manufactured by ARKRAY, Inc.) is shown.

TABLE 1

| Substance name | Concentration |
| --- | --- |
| HEPES | 50 mmol/L |
| 2-Amino-2-methyl-1-propanol (AMP) | 50 mmol/L |
| D-Mannitol | 284 mmol/L |
| Glycerol 3-phosphate | 5 mmol/L |
| EDTA-2K | 0.8 mmol/L |
| PALP (pyridoxal phosphate) | 0.05 mmol/L |
| Thiabendazole | 0.0001% by mass |
| Piperacillin sodium | 0.0003% by mass |
| Amikacin sulfate | 0.0003% by mass |
| Kanamycin sulfate | 0.0005% by mass |
| Meropenem trihydrate | 0.0005% by mass |
| Osmotic pressure | 355 mOsm/Kg |
| pH 7.4 | |

Using the JCA-BM6050 manufactured by JEOL Ltd., a concentration of ALT in the diluent solution of the collected blood plasma was obtained. This concentration was multiplied by a dilution factor calculated by the method described in (Method 1), and thereby a value in the original blood plasma was obtained. Table 2 shows a measured maximum value (U/L) of this ALT, a measured minimum value (U/L) of ALT, and a difference (U/L) between the measured maximum value and the measured minimum value. U/L represents an amount of enzyme capable of changing 1 µmol of a substrate for one minute at a temperature of 30° C. in 1 L of the specimen, under optimal conditions. The results are summarized in Table 2.

TABLE 2

| | Graduation | Measured maximum value (U/L) of ALT | Measured minimum value (U/L) of ALT | Difference (U/L) between measured maximum value and measured minimum value | |
| --- | --- | --- | --- | --- | --- |
| Method 1 | None | 19.7 | 12.3 | 7.4 | Comparative Example 1 |
| | Marked (Specification 1) | 16.5 | 13.4 | 3.1 | Example 1 |
| | Marked (Specification 2) | 15.9 | 13.3 | 2.6 | Example 2 |

Based on the results in Table 2, it was found that in a case where the cylinder had the graduation, the difference between the measured maximum value and the measured minimum value was reduced, and therefore the effect of the present invention was confirmed.

Example 2

A diluted blood plasma solution was prepared in the same manner as in Example 1, and a dilution factor was obtained according to Method 2, Method 3, and Method 4, in addition to Method 1.

(Method 2)

Figure 6:
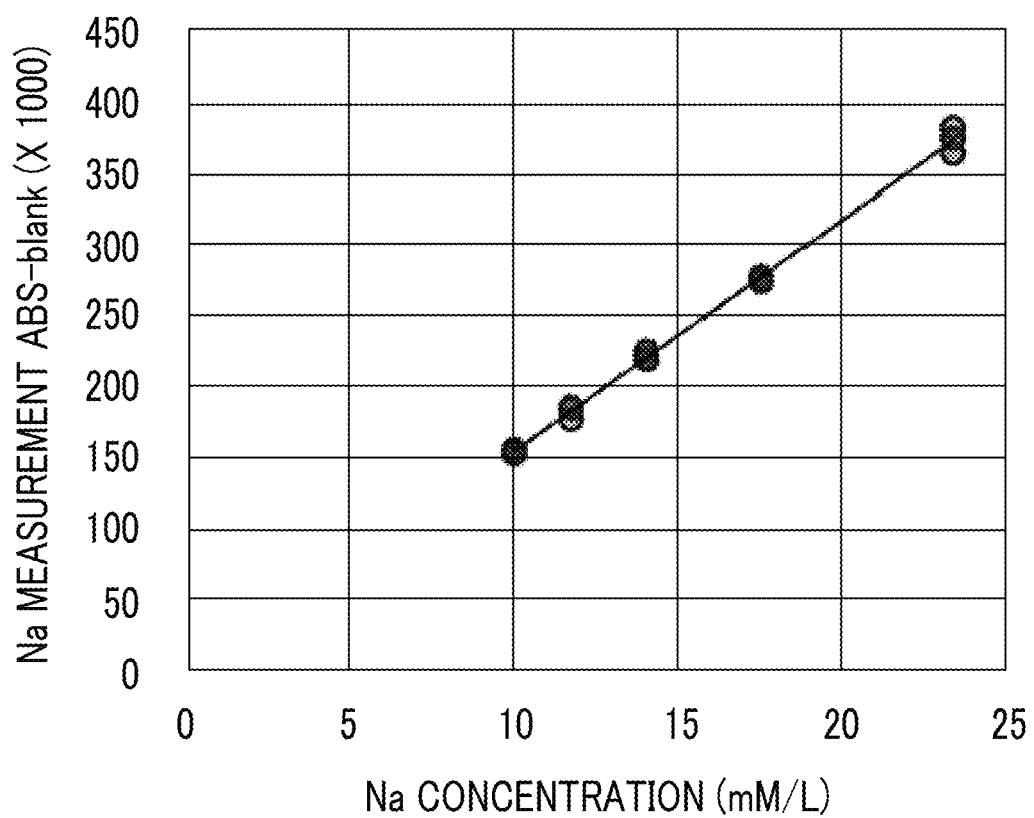
FIG. 6 illustrates the linearity in a sodium enzymatic assay.

A mixed solution of the blood plasma components of the collected blood and the diluent solution was prepared, and a concentration of sodium ion in the mixed solution was measured, and a dilution factor was calculated from this value and a concentration value with respect to 142 mmol/L of a concentration of sodium ions which are usually evaluated as a homeostatic substance. Specifically, some of the mixed solution of the blood plasma components and the diluent solution was diluted 5-fold with purified water and then 3 μl was weighed. 52 μl of a first reagent of a sodium ion measurement reagent shown in Table 3 was added thereto, the mixture was kept at 27° C. for 5 minutes. Next, 26 μl of a second reagent of a sodium ion measurement reagent, which is a substrate solution was added thereto, and then the change in absorbance was obtained by measuring an absorbance during 1 minute at a main wavelength of 410 nm and a complementary wavelength of 658 nm by using JCA-BM6050-type automatic biochemistry analyzer manufactured by JEOL Ltd. FIG. 6 illustrates a calibration curve showing a concentration of sodium and an amount of absorbance change. Linearity in which the line passes through the original point up to 24 mmol/L was obtained, and the quantitativeness of sodium was confirmed. In this Method 2, the preparation was performed while noting that all of the diluent solution shown in Table 1, and the first reagent and the second reagent of the sodium ion measurement reagents shown in Table 3 below does not contain sodium ions.

TABLE 3

Composition of sodium ion measurement reagents

| | Reagent | Concentration |
|---|---|---|
| First reagent | pH 8.0, HEPES/LiOH | 100 mmol/L |
| | D-Mannitol | 60 mmol/L |
| | N-acetylcysteine | 30 mmol/L |
| | Magnesium sulfate | 1.52 mmol/L |
| | β-galactosidase | 1.1 kU/L |
| | TRITON (registered trademark) X-100 | 0.05% by mass |
| Second reagent | pH 8.0, HEPES/LiOH | 100 mmol/L |
| | o-Nitrophenyl β-D-galactopyranoside | 15 mmol/L |

(Method 3)

According to the method disclosed in "Clinicopathology Vol. 56, No. 7 (July 2008) Supplement 577-583" (JP2001-330603A), by using the absorbance which is an index of a concentration of glycerol 3-phosphate added to the diluent solution, a dilution factor of blood was obtained according to the method disclosed in (JP2001-330603A). A reagent used for coloring glycerol 3-phosphate was also designed in the same manner as in Method 2 while noting that the solution of JP2001-330603A does not contain sodium ions.

(Method 4)

Using the values obtained using Method 2 and Method 3, a dilution factor of the diluent solution of blood plasma was obtained from Formula (1).

$$X=(A+C)/(B+D) \tag{1}$$

A: Measurement absorbance of the diluent solution containing glycerol 3-phosphate measured in Method 3

B: Absorbance obtained by subtracting an absorbance of the diluent solution by which blood plasma components are diluted from the absorbance of A C: Measured absorbance of a solution in which a concentration of sodium ions, as a homeostatic substance, is 142 mmol/L D: Absorbance of a concentration of sodium ions in the diluent solution by which the blood plasma component are diluted X: Dilution factor of blood plasma The dilution factor obtained as above was multiplied by the concentration of AST in the diluted blood plasma obtained using JCA-BM6050 manufactured by JEOL Ltd., and thereby AST present in the blood plasma was obtained. The same measurement was repeated ten times to obtain a measured maximum value (U/L) of ALT, a measured minimum value (U/L) of ALT, and a difference (U/L) between the measured maximum value and the measured minimum value. The results are shown in Table 4. U/L represents an amount of enzyme capable of changing 1 μmol of a substrate for one minute at a temperature of 30° C. in 1 L of the specimen, under optimal conditions. The results are shown in Table 2.

TABLE 4

| | Graduation | Measured maximum value (U/L) of AST | Measured minimum value (U/L) of AST | Difference (U/L) between measured maximum value and measured minimum value | |
|---|---|---|---|---|---|
| Method 1 | None | 45 | 23.1 | 21.9 | Comparative Example 1 |
| Method 2 | None | 38.9 | 30.3 | 8.6 | Comparative Example 2 |
| | Marked (Specification 1) | 36.9 | 32.4 | 4.5 | Example 3 |
| | Marked (Specification 2) | 35.5 | 31.8 | 3.7 | Example 4 |

TABLE 4-continued

| | Graduation | Measured maximum value (U/L) of AST | Measured minimum value (U/L) of AST | Difference (U/L) between measured maximum value and measured minimum value | |
|---|---|---|---|---|---|
| Method 3 | None | 38.7 | 30.8 | 7.9 | Comparative Example 3 |
| | Marked (Specification 1) | 36.0 | 31.7 | 4.3 | Example 5 |
| | Marked (Specification 2) | 35.6 | 32.1 | 3.5 | Example 6 |
| Method 4 | None | 38.6 | 31.0 | 7.6 | Comparative Example 4 |
| | Marked (Specification 1) | 34.6 | 31.1 | 3.5 | Example 7 |
| | Marked (Specification 2) | 35.1 | 32.1 | 3.0 | Example 8 |

Based on the results, it was found that in a case where the cylinder had the graduation, the difference between the measured maximum value and the measured minimum value was reduced, and therefore the effect of the present invention was confirmed. Furthermore, in a case where a dilution factor was calculated using the internal standard and the external standard so as to correct the measurement value, it was confirmed that the difference between the maximum value and the minimum value was significantly reduced. In addition, in Method 4, in a case where a dilution factor was obtained using Formula 2 so as to correct the measurement value, the same effect as in Method 4 was obtained.

Example 3

Measurement was carried out in the same manner as in Example 1 except that marks (graduations) that serve as an indication of a liquid volume after blood serum separation were omitted in the cylinder used in Specification 2 of Example 1, and instead, the graduation, which is the same as that of Specification 2, capable of measuring an increase in a liquid volume was marked on a mandrel portion of a sealing cap for preventing back flow of the separated solution.

Example 4

In addition to the measurement of a concentration of sodium ion, a concentration of the total protein was measured on the mixed solution of the blood plasma components collected in Method 2 of Example 2 and the diluent solution by using the following method.

(Measurement of Concentration of Total Protein in Mixed Solution of Diluted Blood Plasma)

Measurement using the biuret method as the measurement principle was performed. Biuret reagent: 3.0 mmol/L, copper sulfate 400 μl, potassium sodium tartrate 21.3 mmol/L, and NaOH 0.75 mol/L were prepared and mixed with the diluted blood plasma. After mixing, the mixture was left alone at 37° C. for 10 minutes, and it was waited until a complex exhibiting blue-violet color of 540 to 560 nm due to protein and copper ions in blood plasma under an alkaline environment was formed, the absorbance was measured at 545 nm, and therefore, a concentration of total protein in the mixed solution of diluted blood plasma was quantitatively determined using a calibration curve obtained from the absorbance of a standard solution.

The result in which a dilution factor (Y/X) of a blood sample obtained from a measurement value (concentration X) of a concentration of sodium ions in a diluent solution after diluting the blood, and a known concentration value (concentration Y; 142 mmol/L) of sodium ions, which is a normal component of the blood sample, is the same value as a dilution factor obtained from a measurement value of total protein in a diluent solution after diluting the blood, and a known concentration value (concentration; 7.5 g/100 mL) of total protein, which is a normal component of the blood sample, was obtained. Based on the result, it was found that it was possible to verify that the measurement of the dilution factor obtained from a concentration of sodium ions was performed normally.

Example 5

In the completely same manner as in Example 1, it was possible to confirm the characteristics with less variation of the present invention, regarding the following blood test items.
<Test Item>
Total protein, albumins, γ-glutamyl transferase, total cholesterol, neutral fat, good cholesterol, urea nitrogen, creatine, uric acid, blood glucose, glycohemoglobin, p53 antibody (tumor marker), CEA (carcinoembryonic antigen), CA125 (cancer antigen 125: ovarian cancer tumor marker), pepsinogen, AFP (α fetoprotein: liver cancer tumor marker), CA19-9 (carbohydrate antigen 19-9; pancreatic/gallbladder cancer marker), *Helicobacter pylori*, HIV (human immunodeficiency virus) antibody, HBs antigen (protein outside of hepatitis B virus), HCV (hepatitis C virus) antigen.

Example 6

An internal standard-added diluent solution which does not contain sodium ions and in which glycerol 3-phosphate was changed to 1 mmol/L of lithium chloride in the composition of Table 1, was prepared. The measurement of the lithium internal standard substance added to the buffer solution can be obtained by measuring the absorbance by using the chelate colorimetric method (halogenated porphyrin chelating method: perfluoro-5,10,15,20-tetraphenyl-21H,23H-porphyrin).

EDTA was added to the blood collected from a plurality of patients to prevent blood coagulation. A small volume of blood collected using the cylinder and the sponge-like tip of Specification 2 which were used in Example 1 was diluted with a diluent solution. Thereafter, the biochemical components in the diluted blood plasma obtained by separating the blood cells by the separation membrane were measured. Separately, a dilution factor of blood plasma was obtained in the same manner as in Method 4 of Example 1 except that A was used as the absorbance of the lithium buffer solution, and B was used as the change in the absorbance of lithium after mixing the blood plasma with the diluent solution in Method 4 of Example 1. The dilution factor was multiplied by the value of the biochemical components in the diluted blood plasma obtained separately, and therefore a value (A) of the biochemical components originally present in the blood plasma was acquired. Separately, a value (B) of the biochemical components of undiluted blood plasma obtained by separating blood cells by centrifugation in the same blood specimen collected after adding EDTA, was obtained. Correlation coefficients of two values each obtained from patients were calculated using the following formula.

Correlation coefficient=(covariance of value (*A*) and value (*B*))/{(standard deviation of value (*A*))× (standard deviation of value (*B*))}     (2)

As the correlation coefficient becomes closer to 1.000, this shows that the two data matches, and 0.800 or more generally shows favorable correlativity. In addition, a scatter diagram was prepared from two data and a regression formula (y=ax±b) was obtained from the distribution as a statistical numerical formula by using the least squares method. The "a" is the slope of the regression formula, and "a" being within the range of 0.95 to 1.05 shows that the proportionality of the two data is favorable. The "b" is the intercept of the regression formula, and "b" being a numerical value close to 0 shows that the error is small. The results are shown in Table 5.

TABLE 5

Correlativity of biochemical tests between diluted blood plasma and blood plasma by Li internal and external standard method
Correlativity between blood plasma and diluted blood plasma in internal and external standard method

| Item | Correlation coefficient | Regression formula (y = ax ± b) |
| --- | --- | --- |
| Total protein | 0.751 | y = 0.98x + 1.4 |
| Albumins | 0.822 | y = 0.97x + 0.6 |
| AST (aspartate aminotransferase) | 0.990 | y = 0.98x + 0.5 |
| ALT (alanine transaminase) | 0.998 | y = 1.00x − 0.1 |
| γ-GTP (γ-glutamyl transpeptidase) | 0.998 | y = 1.02x − 0.6 |
| Total cholesterol | 0.973 | y = 0.97x + 5.6 |
| HDL (high density lipoprotein) cholesterol | 0.987 | y = 0.97x + 1.5 |
| LDL (low density lipoprotein) cholesterol | 0.990 | y = 0.98x + 3.3 |
| Neutral fat | 0.999 | y = 1.05x − 3.8 |
| Urea nitrogen | 0.993 | y = 0.99x + 0.1 |
| Creatine | 0.966 | y = 0.98x + 0.0 |
| Uric acid | 0.994 | y = 1.01x + 0.0 |
| Glucose | 0.994 | y = 0.97x + 2.0 |

Based on the results in Table 5, it was found that the correlativity between the value obtained from the blood plasma diluted using the blood test kit of the present invention and the value obtained from the blood plasma not diluted shows favorable results.

EXPLANATION OF REFERENCES

1: blood separating instrument
2: blood collection container
3: tubular body
4: cap piston
5: sealing lid
6: cap
7: packing
8: screw portion
9: locking portion
10: bottom portion
11: leg portion
12: slit grooves
13: diluent solution
14: expanded diameter section
15: thin wall portion
16: main body portion
18: reduced diameter section
19: protruded locking portion
20: outer flange portion
21: filtration membrane
22: cover
26: knob portion
27: mandrel portion
28: space
29: lower end portion
31: level difference portion
33: upper end portion
34: top portion
101: transparent cylinder
102: gasket
103: blood cells
104: transparent cylinder
105: blood plasma
106: back flow prevention valve
107: sealing cap
108: mandrel portion
109: graduations
110: graduation of diluent solution
201: cylinder
202: graduation
203: back flow prevention valve
204: narrow portion
205: thick portion
206: graduation of diluent solution

What is claimed is:

1. A blood test kit, comprising:
a diluent solution for diluting components of a blood sample; and
at least one transparent container for storing the components of the blood sample and the diluent solution,
wherein the blood test kit is for analyzing a concentration of a target component in the components of the blood sample by using a normal component homeostatically present in the blood, and the blood test kit is for verifying the analysis by using another normal component homeostatically present in the blood that is different from the normal component, and
the diluent solution does not contain sodium ions,
wherein at least one constituent component included in the blood test kit is marked with a graduation for measuring a liquid volume of the components of the blood sample and the diluent solution.

2. The blood test kit according to claim 1,
wherein the diluent solution contains a normal component not present in the blood, and
the blood test kit is for analyzing a concentration of the target component in the components of the blood sample by using the normal component not present in the blood.

3. A blood test kit, comprising:
a diluent solution for diluting components of a blood sample; and
at least one transparent container for storing the components of the blood sample and the diluent solution,
wherein the blood test kit is for analyzing a concentration of a target component in the components of the blood sample by using a normal component homeostatically present in the blood, and by using a normal component not present in the blood, and
the diluent solution contains lithium chloride, but does not contain sodium ions,
wherein at least one constituent component included in the blood test kit is marked with a graduation for measuring a liquid volume of the components of the blood sample and the diluent solution.

4. The blood test kit according to claim 3,
wherein the blood test kit is for analyzing a concentration of the target component in the components of the blood sample by using a normal component homeostatically present in the blood and for verifying the analysis, and
the diluent solution does not contain the normal component.

5. The blood test kit according to claim 1,
wherein the graduation includes at least a graduation for measuring a liquid volume of a diluent solution which does not contain the components of the blood sample.

6. The blood test kit according to claim 1,
wherein the constituent component is at least one transparent container for storing the components of the blood sample and the diluent solution.

7. The blood test kit according to claim 6,
wherein the transparent container has a portion of which an interior cross-sectional area is smaller than that of other portions, and the portion of which the interior cross-sectional area is smaller than that of other portions is marked with the graduation.

8. The blood test kit according to claim 7,
wherein a portion of which an interior cross-sectional area in the transparent container is smallest is marked with the graduation.

9. The blood test kit according to claim 1,
wherein the components of the blood sample are blood plasma components separated from the blood sample by a separation means.

10. The blood test kit according to claim 1,
wherein the normal component homeostatically present in the blood is a component selected from the group consisting of sodium ions, chloride ions, total protein, and albumins.

11. The blood test kit according to claim 3,
wherein the normal component not present in the blood is lithium.

12. The blood test kit according to claim 1,
wherein the diluent solution is a buffer solution having a buffering action within a pH range of pH 6.5 to pH 8.0.

13. The blood test kit according to claim 1,
wherein the diluent solution is a diluent solution including an amino alcohol compound selected from the group consisting of 2-amino-2-methyl-1-propanol, 2-ethylaminoethanol, N-methyl-D-glucamine, diethanolamine, and triethanolamine, and including a buffering agent selected from the group consisting of 2-[4-(2-hydroxyethyl)-1-piperazinyl]ethanesulfonic acid also called HEPES, N-tris(hydroxymethyl)methyl-2-aminoethanesulfonic acid also called TES, 3-morpholinopropane sulfonic acid also called MOPS, and N,N-bis(2-hydroxyethyl)-2-aminoethanesulfonic acid also called BES.

* * * * *